US007027233B2

United States Patent
Goldstein et al.

(10) Patent No.: US 7,027,233 B2
(45) Date of Patent: Apr. 11, 2006

(54) CLOSED-LOOP FOCAL POSITIONING SYSTEM AND METHOD

(75) Inventors: Peter Goldstein, Santa Ana, CA (US); Carlos G. Suarez, Irvine, CA (US); Scott A. DeLong, Escondido, CA (US); R. K. Webb, Escondido, CA (US); Tibor Juhasz, Irvine, CA (US)

(73) Assignee: Intralase Corp., Irvine, CA (US)

( * ) Notice: Subject to any disclaimer, the term of this patent is extended or adjusted under 35 U.S.C. 154(b) by 0 days.

(21) Appl. No.: 10/827,837

(22) Filed: Apr. 20, 2004

(65) Prior Publication Data

US 2004/0228013 A1   Nov. 18, 2004

Related U.S. Application Data

(63) Continuation-in-part of application No. 09/976,555, filed on Oct. 12, 2001, now Pat. No. 6,751,033.

(51) Int. Cl.
   *G02B 15/14* (2006.01)
(52) U.S. Cl. .................................. 359/697; 359/696
(58) Field of Classification Search ........ 359/821–824, 359/697–698, 6; 702/94, 95; 356/6
   See application file for complete search history.

(56) References Cited

U.S. PATENT DOCUMENTS

| | | | | |
|---|---|---|---|---|
| 4,002,899 A * | 1/1977 | Stauffer | ............... | 250/201.8 |
| 4,450,358 A | 5/1984 | Reynolds | ............... | 205/492.1 |
| 4,700,056 A * | 10/1987 | Silvy et al. | ............... | 369/44.28 |
| 4,786,124 A * | 11/1988 | Stone et al. | ............... | 359/15 |
| 4,899,327 A | 2/1990 | Bates et al. | ............... | 369/44.35 |
| 4,935,763 A * | 6/1990 | Itoh et al. | ............... | 396/81 |
| 4,984,000 A * | 1/1991 | Watanabe et al. | ............... | 396/87 |
| 5,161,165 A * | 11/1992 | Zorabedian | ............... | 372/20 |
| 5,247,153 A | 9/1993 | Pasch | ............... | 219/121.68 |
| 5,475,209 A * | 12/1995 | Nabeshima | ............... | 250/201.4 |
| 5,696,589 A * | 12/1997 | Bernacki | ............... | 356/630 |
| 5,768,226 A | 6/1998 | Ogino | ............... | 369/44.28 |
| 5,923,473 A | 7/1999 | Kelley et al. | ............... | 359/618 |
| 6,043,843 A | 3/2000 | Kelley et al. | ............... | 348/335 |
| 6,160,910 A | 12/2000 | Freifeld | ............... | 382/154 |
| 6,304,359 B1 | 10/2001 | Gadhok | ............... | 359/198 |
| 6,325,793 B1 | 12/2001 | Tomita | ............... | 606/4 |
| 6,462,814 B1 | 10/2002 | Lo | ............... | 356/237.2 |
| 6,483,071 B1 | 11/2002 | Hunter et al. | ............... | 219/121.6 |
| 2004/0170312 A1* | 9/2004 | Soenksen | ............... | 382/133 |

* cited by examiner

*Primary Examiner*—Ricky Mack
(74) *Attorney, Agent, or Firm*—Connolly Bove Lodge & Hutz LLP (57) ABSTRACT

A closed-loop focusing system and method positions a focusing assembly to a desired positioned. A feedback positioning device, such as a linear encoder, provides an actual or "read" value for the linear movement of the focusing assembly. The desired position is compared to the actual position of the focusing assembly. If the two values are outside of a predetermined tolerance or valid range, then an audible or visual warning will be given. When a laser source is utilized with the focusing system, laser operation will be prevented if the two values are outside of an acceptable range. However, if the difference between the desired position and the actual position are within an acceptable range, the focusing assembly is repositioned to allow real-time systematic correction of the position of the focusing assembly.

46 Claims, 5 Drawing Sheets

CLOSED-LOOP FOCAL POSITIONING SYSTEM AND METHOD

This application is a continuation-in-part of application Ser. No. 09/976,555 filed on Oct. 12, 2001, no U.S. Pat. No. 6,751,033.

BACKGROUND OF THE INVENTION

Various laser procedures or operations require that the laser beam be properly focused to a specific focal point. For example, in ophthalmic laser surgery wherein eye tissue is to be photodisrupted or ablated in or on the tissue that is to be affected, the correct positioning of a focusing assembly used to focus a laser beam is very critical. Such ophthalmic surgical procedures include those in cornea, sclera, iris, the crystalline lens and related structures, vitreous, and retina, and for treatment of glaucoma. Focal depth precision is also required in many non-ophthalmic laser surgical procedures, such as applications in dermatology and even "surgery" in DNA to excise portions of chromosomes. Also, non-biologic applications, such as photolithography and micromachining require focal depth precision.

Even with calibration of a focusing element for a laser, which is made to vary according to the requirement of the surgical treatment pattern, the actual focal depth of the laser beam may differ from the desired focal depth for the treatment. Hence, there is a need for a closed-loop system that controls movement of a focusing assembly to a desired position and feedback validation that the desired movement of the focusing assembly has been achieved. In this manner, the depth position of a focal point may be precisely controlled.

SUMMARY OF THE INVENTION

The present invention relates generally to a closed-loop focal positioning system. More particularly, the invention relates to a method and system for moving a focusing assembly for focusing a laser beam to a desired position (also referred to as the theoretical position) and then determining via a feedback positioning device, an actual movement value of the focusing assembly.

Briefly stated, the closed-loop focal positioning system utilizes a computer processor for the execution of software to control the movement of a focusing assembly used to focus a laser beam. The software is configured to allow an operator to identify a laser focal point or depth. In turn, the focusing assembly is instructed to move to a desired position. A feedback positioning device reads the actual position or movement of the focusing assembly. A comparison of the desired position and the actual position is used to determine if the focusing assembly has been correctly moved, thereby ensuring that the laser beam will be correctly focused when it is activated.

In one embodiment, the focusing assembly is repositioned if a delta value, the difference between the desired position and the actual position, are within an acceptable range. This allows systematic correction of the position of the focusing assembly. However, if the delta value falls outside of an acceptable range then the laser system focusing assembly should be recalibrated.

Various laser sources may be used with the inventive system and method, including infrared, visible, and UV lasers. Further, laser sources to be used with the inventive system may be continuous wave, Q-switched pulse, and mode-locked ultrashort pulse lasers. Although the following is not an exhaustive list, lasers of the foregoing type may be used with the present invention. In the preferred embodiment, the laser source is an infrared ultrashort pulse laser with a pulse duration of less than 10 picoseconds.

The focusing assembly may be a single lens, objective lens, compound lens, a lens assembly, curved mirror or series of curved and/or flat mirrors, a combination of the foregoing, or a moveable housing containing the foregoing, that is used to focus a laser beam where the movement of the focusing assembly can be measured and the movement correlated to a focal depth. In other words, the focusing assembly can be any laser focusing device in whole or in part that is moveable, and the movement of such device can be measured by a feedback positioning device to determine if an actual focal point is achieved.

In an embodiment of the inventive system, an operator of a laser system for ophthalmic surgery identifies a desired focal depth position value for photodisruption or ablation of a structure of the eye, such as the cornea or crystalline lens. A software program executing on a host computer receives the value for the laser focal depth position. The software program commands a displacement of a focusing assembly of a laser system by writing a voltage to a Digital/Analog card. A Z galvo will in turn move the focusing assembly to the desired focal depth position based upon the commanded voltage by directing a current to the motor-driven focusing assembly.

A linear encoder positioned within the laser system senses the linear movement of the focusing assembly. An intelligent controller interoperating with the host computer and software program utilizes a sensor to read an encoder strip attached to the focusing assembly. As the lens is moved into position, encoder feedback is provided by an intelligent controller and an actual focusing assembly position is obtained.

Although in one embodiment the feedback positioning device is a linear encoder, other feedback positioning devices may be used including a rotary encoder, an interferometric encoder, an optical encoder, a resolver, a Heidenheim scale, angular encoders, digital length gauge systems, phase device, magnetic strip reader, or transducer.

BRIEF DESCRIPTION OF THE DRAWINGS

For a more complete understanding of the present invention, reference is now made to the following descriptions taken in conjunction with the accompanying drawing, in which:

FIG. 2b is a schematic diagram of an exposed internal view of the focusing assembly of FIG. 2a;

DETAILED DESCRIPTION OF THE INVENTION

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Closed-loop Focal Positioning System

Figure 1:
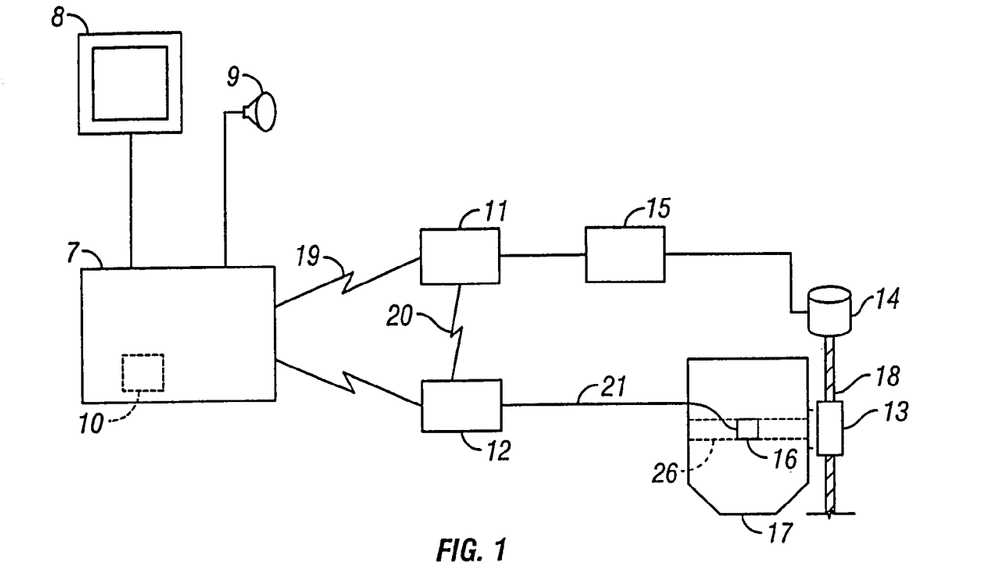
FIG. 1 is a schematic view of the closed-loop focal positioning system illustrating an embodiment of the present invention.

FIG. 1 depicts a schematic view of one embodiment of the closed-loop focusing system according to the present invention. A computer 7 having a CPU 10 on a motherboard is interconnected to a digital to analog converter card 11 by way of a cable 19. The CPU 10 sends instructions to the digital/analog converter card 11 thereby providing a voltage from a power source 15 to a motor 14. The motor provides linear movement of the movable zoom lens assembly 26 (shown in a housing 17) via a drive shaft 18 housed in a drive shaft housing 13. Alternatively, a mirror or series of mirrors may be used as the movable element. A feedback positioning device 12, such as a linear encoder, utilizing a sensor 16, reads the movement of the focusing assembly 26. The feedback positioning device 12 is interconnected with the CPU 10. A monitor or screen 8 and a speaker 9 may be utilized to provide audible and/or visual warnings.

In one embodiment, the focusing assembly is part of a Z galvo motorized focusing system. A Z galvo is generally a limited excursion motor whose torque is directly proportional to the current applied. When current is applied to the motor, the galvo's shaft rotates through part of a circle. As long as the current is applied the shaft will remain rotated in correlation to the amount of current applied. When current is reduced, the shaft rotates toward its original position with the shaft returning to its resting position when current is removed. Based on the amount of current applied to the motor, the focal point of light through the focusing assembly is displaced. In another embodiment, the movable focusing assembly may be a curved mirror or a series of curved and/or flat mirrors whose position determines the laser focal depth position.

In one embodiment, a linear encoder, such as the MicroE Systems™ model (M2100L30SS200) product may be utilized as a feedback positioning device 12. The MicroE encoder product consists of an encoder strip (a glass strip with reflective gradient), a sensor head 16, and interpolator to serial module 12. The encoder is preferably configured for a resolution of 0.1 μm or less per count at a frequency of about 900 kHz or greater.

The CPU utilizes the linear encoder to accurately check the position of the zoom lens assembly and thereby control the focal position to within a few of microns of an absolute value. This is accomplished by knowing the galvo command voltage increments (linear voltage steps that produce linear galvo rotation). The galvo produces precise rotational motion of the lead screw that actuates the movement of the focusing assembly. An optical encoder gradient strip is attached to the focusing assembly. The encoder, therefore, accurately measures the movement of the focusing assembly. With knowledge of the encoder output (a number of counts per micron of movement) and the galvo voltage step command (the number of voltage steps per micron of movement) the system software can compare the two and determine if the condition is normal or out of range.

Figure 2A:
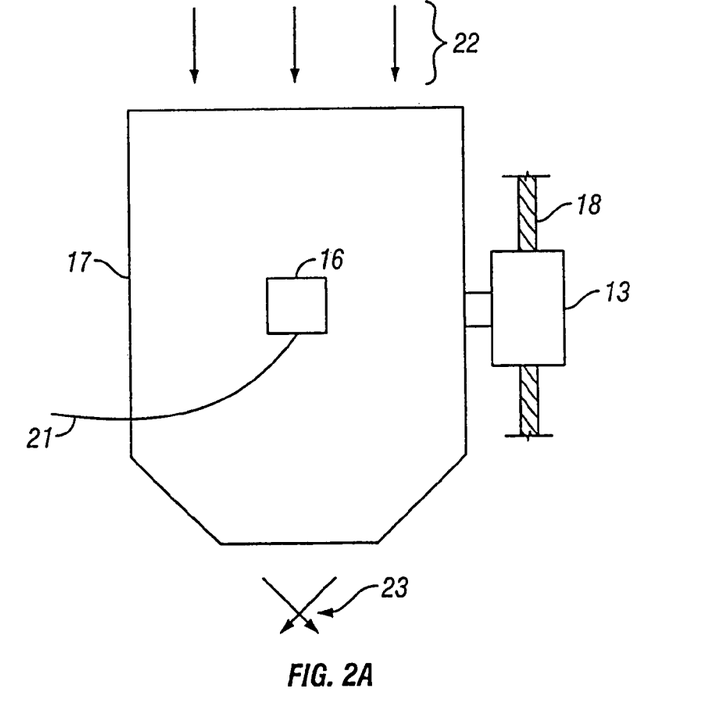
FIG. 2a is a schematic diagram view of a focusing assembly used with the present invention.
Figure 2B:
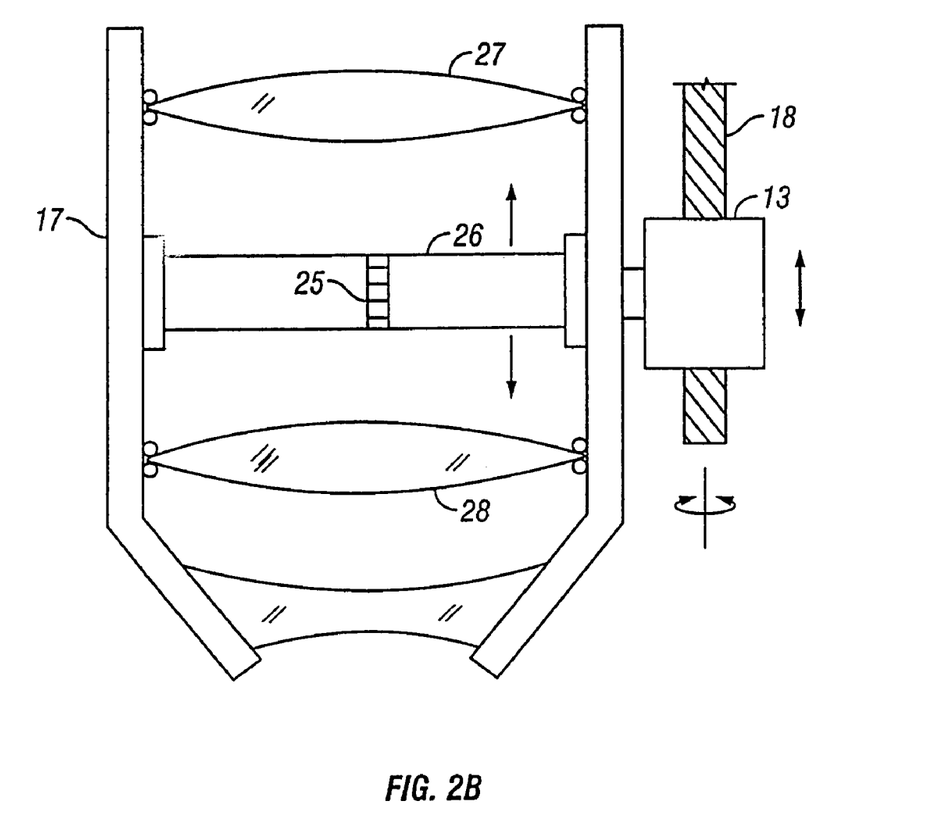
Figure 2C:
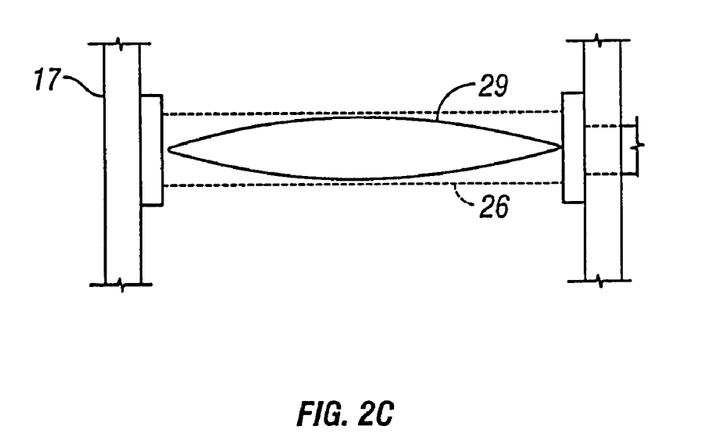
FIG. 2c is a schematic diagram of an exposed internal view of the moveable zoom lens assembly of FIG. 2b.
Figure 3:
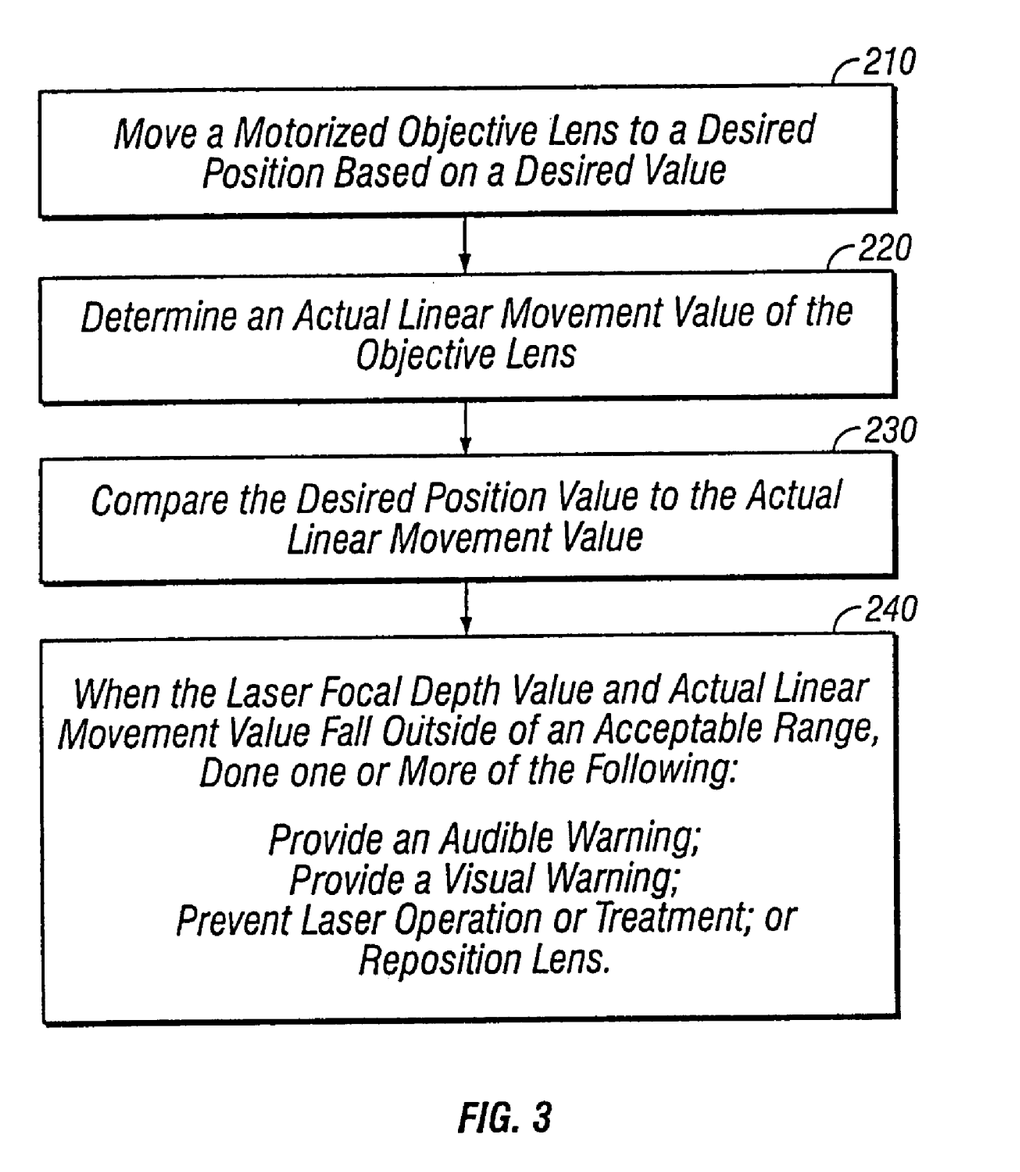
FIG. 3 is a flowchart illustrating a method of laser focusing depth validation.

As further illustrated in FIGS. 2a–2c, the sensor head 16 is affixed to the housing 17 where a window or opening in the housing 17 exists so that the sensor head 16 can read a gradient strip 25 affixed to the focusing assembly 26. As the focusing assembly 26 is moved or moves in a linear fashion the sensor head 16 reads the movement of the focusing assembly 26. The focusing assembly as depicted in the Figures is used to focus a laser beam 22 to a fixed focal point 23 in conjunction with other optical elements 27, 28 and 29.

A quadrature (A, B, and Index) to serial RS-232 converter, model #AD4-B-D-S1767 from U.S. Digital, may be utilized as a digital/analog converter card 11. The AD4-B board is preferably connected to a computer 7 motherboard via a nine pin cable 19 running at a standard 9600 baud.

The MicroE interpolator 12 and the U.S. Digital board 11 are mounted together as an assembly. Power is provided to the assembly via a DC plug that plugs into the U.S. digital board from the computer system power supply +12 VDC. The interpolator and AD4-B board are connected via cable 20. The quadrature signals are passed to the U.S. Digital board 11 from the MicroE interpolator via RS-422 (differential). Also power is provided to the MicroE board via a power cable. The MicroE sensor head 16 is attached to the housing 17 via a cable 21 from the interpolator 12. The encoder glass strip 25 is attached to the focusing assembly 26 with a UV cured adhesive.

The computer 7 controls positioning of the focusing assembly 26 and receives data pertaining to the position of the focusing lens assembly from the interpolator 12.

Software Control of the Closed-loop Focal Positioning System

In one embodiment of the inventive system, the focal position is computed and controlled via software instructions preferably executable via a CPU 10. The software instructions may be contained on storage media such as CDs, hard drives, diskettes, or other electronic storage media devices. Additionally, the computer software (instruction sets) may be stored in ROM, RAM or other storage devices capable of storage computer instructions. The software program may be configured to provide various control of the focusing assembly 26. Functions performed by the software may include: Initialization of the System, Calibration of the System, Movement of the Focusing Assembly, Automatic Repositioning of the Focusing Assembly, and Determination that the Focusing Assembly is at a Desired Position. Based on this disclosure other functions would be readily ascertainable to one skilled in the art.

Initialization of the System. An initialization and error checking process is performed to determine whether individual components of the system are operable. A status or response is requested from the component devices .such the focusing assembly (e.g., the Z galvo objective lens), the analog-to-digital converter, linear encoder and the communication ports. Should any of these devices respond with an error code or not respond at all then the software will indicate such an error.

Calibration of the System. The software checks the linear encoder index affixed to the focusing assembly. In one embodiment, a Z galvo is commanded to move through its upper and lower limits and a zero position is established. The Z galvo is then parked or stopped at a zero position. Additionally, the software. calibrates the Z galvo. by submitting a signal to a digital to analog converter, which in turn provides positive and negative voltage signals to the Z galvo. After the Z galvo is instructed to move a reading is taken from the encoder index.

Movement of the Focusing Assembly. After calibration of the Z galvo, positioning commands are made to move the, Z galvo to the desired position. Initially, the Z galvo begins at a zero position. The Z galvo focusing assembly is commanded to move to desired positions. With the linear encoder, the actual position of the focusing assembly is then determined.

Determination that the Focusing Assembly is at a Desired Position. Once the Z galvo is moved to a desired position, the actual position of the Z galvo is determined. An encoder sensor reads the encoder index through a housing window.

The software program compares the actual focusing assembly position to the desired focal depth position. The software determines whether the desired focal depth position is within a certain range. If the actual focusing assembly position and the desired focal depth position are within range, then the software will allow the laser treatment of the eye to continue. If the actual focusing assembly position is out of range, then the software will prevent laser treatment from commencing.

An acceptable range may be configured according to the particular uses of the focusing system. In the context of ophthalmic surgery, the differences between the desired position and the actual position should be typically 5 microns or less. This assures that the positioning of the lens and subsequent treatment of the eye structure will be extremely accurate. For example, an acceptable range can be set as follows:

If the D<=X, where D is the difference between the desired position and actual position, X is 5 microns or less, then no lens adjustment is made and laser treatment is allowed;

If the X<D<Y, where Y is 25 microns, then readjust the focusing assembly to reduce the difference between X and Y, and reconfirm proper X value; and If D>=Y, then the focusing assembly needs to be recalibrated and no laser treatment should occur.

In the closed-loop focusing system of the present invention, movement of the lens may achieved in number of ways, including, but not limited to, the following:

1. A computer processor may instruct a motorized focusing assembly to linearly move the assembly to a desired position from a base position. The processor interconnected with a digital-to-analog converter provides a voltage source to the motorized lens thereby moving the lens to the desired position. A feedback positioning device then determines the actual position of the lens.

2. Additionally, the computer processor may instruct movement of the focusing assembly when the focusing assembly is not positioned at its base position. For example, the computer processor may have previously moved the focusing assembly to a desired position. The focusing assembly would be moved to the new position without having to return to the base position. The value of the current position and the new desired position are used to calculate how much the focusing assembly should be positioned.

3. The focusing assembly may also be commanded to move by specific increments by the operator of the system. For example, the assembly may be commanded to move up or down by specific increments, such as microns.

Automatic Repositioning of the Focusing Assembly. A delta value can be computed as the absolute difference between the desired position value and the actual position value. The delta value can then be compared to an acceptable range of variance between the desired position and the actual: position. If the delta value is slight, say about plus or minus 2 microns, then the focusing assembly would not be repositioned. However, if a greater delta value exists, say between >2 microns to <25 microns, then the focusing assembly would be slightly repositioned so that the difference between the desired positioned and actual position is plus or minus 2 microns. If the variance is greater than 25 microns, than the focusing assembly should be recalibrated. The accuracy needed for repositioning the focusing assembly would depend on the particular application. The system may be configured such that the repositioning of the focusing assembly is completed at the end of each instructed movement. Alternatively, during the movement of the focusing assembly the feedback positioning device can monitor an actual position and compare it with the position where the system estimates the position of the focusing assembly. In this manner, corrective action can be taken immediately and the focusing assembly repositioned real-time if the delta value falls outside of an acceptable range.

Exemplary Implementation of the Closed-loop Focal Positioning System

Figure 4:
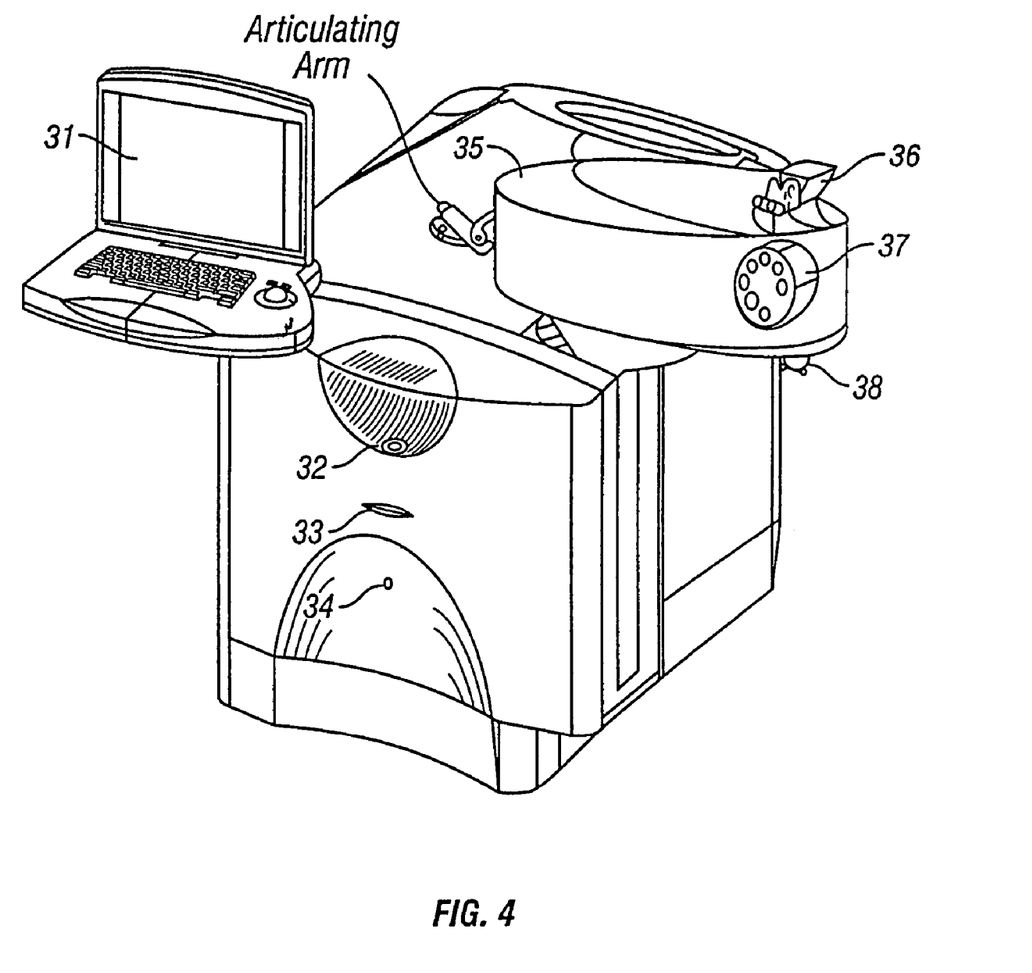
FIG. 4 is a perspective view of an exemplary ophthalmic laser system in which the present inventive system may be implemented.

Referring to FIG. 4, a perspective view of an exemplary ophthalmic laser system in which the present inventive system may be implemented is shown. A user interface and terminal 31 provides for data input into a CPU (not shown) of desired focal values. The exemplary ophthalmic laser system includes an emergency shut off switch 32, disk drive 33, key switch 34, beam delivery device 35, operating microscope 36, control panel 37, and a loading deck for interface to an eye-stabilizing device.

Figure 5:
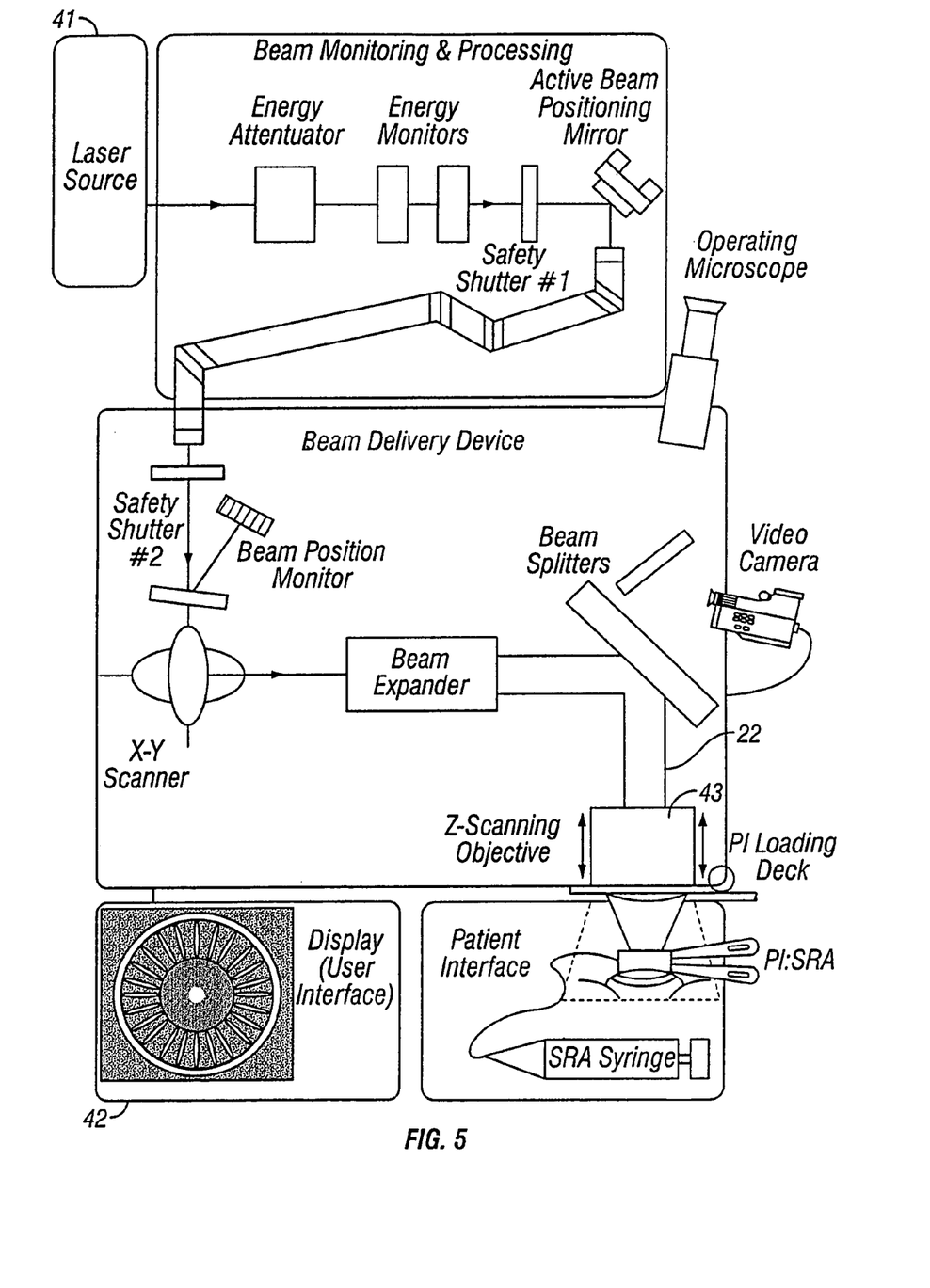
FIG. 5 is a schematic view of an exemplary ophthalmic laser system in which the present inventive system may be implemented.

Referring to FIG. 5, a schematic view of the exemplary ophthalmic laser system of FIG. 4 is shown. A laser source 41 is directed through a beam delivery device into a z-scanning objective lens 43. A display 42 is provided for viewing the eye undergoing laser treatment. The display may provide visual warning to the operator of the system when the focusing assembly falls outside of an acceptable range.

The inventive systems and methods described above are well adapted for a closed-loop focal positioning system. However, it shall be noted that the foregoing description is presented for purposes of illustration and description, and is not intended to limit the invention to the form disclosed herein. Consequently, variations and modifications to the systems and processes commensurate with the above teachings and teaching of the relevant art are within the scope of the invention. For example, as mentioned previously, several aspects of the invention may be adapted for application or implementation onto an interactive computer network or client-server system other than the Internet. These variations will readily suggest themselves to those skilled in the relevant art and are encompassed within the spirit of the invention and the scope of the following claims.

Moreover, the embodiments described are further intended to explain the best modes for practicing the invention, and to enable others skilled in the art to utilize the invention in such, or other, embodiments and with various modifications required by the particular applications or uses of the present invention. It is intended that the appending claims be construed to included alternative embodiments to the extent that it is permitted by the prior art.

What is claimed is:

1. A closed-loop focal positioning system, said system comprising:
   a focusing assembly for focusing a laser beam to a focal depth position;
   a feedback positioning device for determining the position of said focusing assembly; and
   a computer processor interconnected to said feedback positioning device, said processor adapted to instruct movement of said focusing assembly based on a value for a desired focal depth position, and said processor adapted to receive an actual position value of said focusing assembly from said feedback positioning device;
   wherein said feedback positioning device is adapted to read the linear movement of the focusing assembly to obtain said actual position value, and said processor is adapted to compute a delta value between said actual position value and said desired position value, and said processor is adapted to reposition said focusing assembly if the delta value is within an acceptable range.

2. The system of claim 1, wherein the feedback positioning device is a linear encoder.

3. The system of claim 1, wherein the feedback positioning device is a rotary encoder.

4. The system of claim 1, wherein the feedback positioning device is an interferometric encoder.

5. The system of claim 1, wherein the feedback positioning device is an optical encoder.

6. The system of claim 1, wherein the feedback positioning device is a resolver.

7. The system of claim 1, wherein the feedback positioning device is a Heidenheim scale.

8. The system of claim 1, wherein the feedback positioning device is an angular encoder.

9. The system of claim 1, wherein the feedback positioning device is a digital length gauge system.

10. The system of claim 1, wherein the feedback positioning device is a phase device.

11. The system of claim 1, wherein the feedback positioning device is a magnetic strip reader.

12. The system of claim 1, wherein the feedback positioning device is a transducer.

13. The system of claim 1, wherein the focusing assembly is a moveable zoom lens.

14. The system of claim 1, wherein the focusing assembly is a galvo-motorized focusing assembly.

15. The system of claim 1, further comprising a digital/analog converter for translating electronic signals from said computer processor to an analog voltage source for powering said moveable focusing assembly.

16. The system of claim 1, further comprising a laser source for generating a laser beam to be directed through said moveable focusing assembly.

17. The system of claim 16, wherein said processor is adapted to permit activation of the laser source if said delta value is within an acceptable range.

18. The system of claim 16, wherein said laser source is a continuous wave, Q-switched pulse, or mode-locked ultrashort pulse laser.

19. The system of claim 1, further comprising a visual display for providing a visual warning to an operator if the delta value is outside of said acceptable range.

20. The system of claim 1, further comprising an audio device for providing an audible warning to an operator when said delta value is outside of said acceptable range.

21. The system of claim 1, wherein said processor is adapted to prevent laser activation if said delta value is outside of an acceptable range.

22. The system of claim 1, wherein said processor is adapted to repeatedly reposition said focusing assembly during movement of the focusing assembly to said desired focal depth.

23. The system of claim 2, wherein said linear encoder comprises an encoder strip, a sensor head and interpolator-to-serial module.

24. A closed-loop focal positioning system, said system comprising:
   a focusing assembly for focusing a laser beam to a focal depth position;
   a feedback positioning device for determining the position of said focusing assembly;
   a computer processor interconnected to said feedback positioning device, said processor adapted to instruct movement of said focusing assembly based on a value for a desired focal depth position, and said processor adapted to receive an actual position value of said focusing assembly from said feedback positioning device; and
   a laser source for generating a laser beam to be directed through said moveable focusing assembly, wherein said laser source is an infrared, ultrashort pulse laser with a pulse duration of less than 10 picoseconds;
   wherein said feedback positioning device is adapted to read the linear movement of the focusing assembly to obtain said actual position value, and said processor is adapted to compute a delta value between said actual position value and said desired position value, and said processor is adapted to reposition said focusing assembly if the delta value is within an acceptable range.

25. A method of positioning a focusing assembly for focusing a laser, said method comprising:
   moving a focusing assembly to a desired position based on a desired position value;
   determining an actual position value for the actual linear movement of said focusing assembly;
   determining a delta value between said actual position value and said desired position value; and
   repositioning said focusing assembly if said delta value is within a particular range.

26. The method of claim 25, wherein the step of moving a focusing assembly to a desired position based on a desired position value comprises:
   receiving by a software program a desired focal depth for a laser beam;
   converting the focal depth value to a position based value; and
   directing said focusing assembly to move to said position based value.

27. The method of claim 26, further comprising the step of preventing activation of said laser beam if said delta value falls outside of an acceptable range.

28. The method of claim 25, wherein the step of determining an actual position value for the actual linear movement of said focusing assembly comprises:
   utilizing a feedback positioning device to read an actual position of the focusing assembly.

29. The method of claim 28, wherein the feedback positioning device is a linear encoder.

30. The method of claim 28, wherein the feedback positioning device is a rotary encoder.

31. The method of claim 28, wherein the feedback positioning device is an interferometric encoder.

32. The method of claim 28, wherein the feedback positioning device is an optical encoder.

33. The method of claim 28, wherein the feedback positioning device is a resolver.

34. The method of claim 28, wherein the feedback positioning device is a Heidenheim scale.

35. The method of claim 28, wherein the feedback positioning device is an angular encoder.

36. The method of claim 28, wherein the feedback positioning device is a digital length gauge system.

37. The method of claim 28, wherein the feedback positioning device is a phase device.

38. The method of claim 28, wherein the feedback positioning device is a magnetic strip reader.

39. The method of claim 28, wherein the feedback positioning device is a transducer.

40. The method of claim 25, wherein the focusing assembly is a moveable zoom lens.

41. The method of claim 25, wherein the focusing assembly is a galvo-motorized focusing assembly.

42. The method of claim 25, further comprising the step of generating a current to a motor for movement of said focusing assembly.

43. The method of claim 25, further comprising the step of providing an audible and/or visual warning that the delta value falls outside of an acceptable range.

44. The method of claim 25, further comprising the step of preventing laser activation if said delta value falls outside of an acceptable range.

45. The method of claim 25, further comprising the step of providing a laser source for generating a laser beam to be directed through said moveable focusing assembly.

46. A method of positioning a focusing assembly for focusing a laser, said method comprising:
  moving a focusing assembly to a desired position based on a desired position value;
  determining an actual position value for the actual linear movement of said focusing assembly;
  determining a delta value between said actual position value and said desired position value; and
  repositioning said focusing assembly if said delta value is within a particular range; and
  providing a laser source for generating a laser beam to be directed through said moveable focusing assembly, wherein the laser source is an infrared, ultrashort pulse laser.

* * * * *